(12) United States Patent
Angelosanto et al.

(10) Patent No.: US 9,645,123 B2
(45) Date of Patent: May 9, 2017

(54) MANIFOLD FOR SOLVENT MIXING IN LIQUID CHROMATOGRAPHY SYSTEMS

(75) Inventors: John Angelosanto, North Attleboro, MA (US); Charles T. Murphy, Norton, MA (US); Kurt Joudrey, Newton, MA (US); Kara O'Donnell, Watertown, MA (US); Paul E. Linderson, Warwick, RI (US); Michael LeBeau, Attleboro, MA (US); Wade P. Leveille, Douglas, MA (US); Michael R. Jackson, Woonsocket, RI (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 1337 days.

(21) Appl. No.: 13/519,833

(22) PCT Filed: Jan. 11, 2011

(86) PCT No.: PCT/US2011/020792
§ 371 (c)(1),
(2), (4) Date: Jun. 28, 2012

(87) PCT Pub. No.: WO2011/085353
PCT Pub. Date: Jul. 14, 2011

(65) Prior Publication Data
US 2012/0287746 A1 Nov. 15, 2012

Related U.S. Application Data

(60) Provisional application No. 61/293,863, filed on Jan. 11, 2010.

(51) Int. Cl.
*G01N 30/32* (2006.01)
*G01N 30/34* (2006.01)
(Continued)

(52) U.S. Cl.
CPC .............. *G01N 30/32* (2013.01); *B29B 7/007* (2013.01); *B29B 7/385* (2013.01); *G01N 30/34* (2013.01);
(Continued)

(58) Field of Classification Search
CPC ... B01F 3/088; B01F 15/00253; G01N 30/32; G01N 30/24; G01N 30/34
(Continued)

(56) References Cited

U.S. PATENT DOCUMENTS 4,280,905 A * 7/1981 Gunkel .................. B01D 15/22
210/198.2
4,427,298 A 1/1984 Fahy et al.
(Continued)

FOREIGN PATENT DOCUMENTS

EP 0240658 10/1987
WO 2005050190 6/2005

OTHER PUBLICATIONS

Kinesis Incorporated, "Vaplock Manifold Stack Units", kinesishplc.com, 2008 (retrieved on Feb. 22, 2011 from http:www.kinesishplc.com/2008_07_01_archive.html), 3 pages.
(Continued)

*Primary Examiner* — Tony G Soohoo
*Assistant Examiner* — Anshu Bhatia
(74) *Attorney, Agent, or Firm* — Schmeiser, Olsen & Watts LLP

(57) ABSTRACT

Low-pressure mixing of fluids includes a pumping system having a pump and a fluidic inlet port through which fluid is introduced to the pump. A fluid proportioning system is in fluidic communication with the fluidic inlet port of the pumping system to deliver thereto a fluid stream comprised of multiple different fluids. The fluid proportioning system includes a manifold having a plurality of inlet ports, an
(Continued)

outlet port connected by tubing to the fluidic inlet port of the pumping system, and an outlet conduit providing an internal fluidic passageway to the outlet port. Each inlet port is fluidically coupled to a fluid source to receive one of the different fluids and to the outlet conduit to deliver thereto the received fluid for delivery out of the manifold through the outlet port to the fluidic inlet port of the pumping system.

19 Claims, 17 Drawing Sheets

(51) Int. Cl.
    *B29B 7/00*     (2006.01)
    *B29B 7/38*     (2006.01)
    *G01N 30/24*     (2006.01)
    *G01N 30/20*     (2006.01)
    *B01D 15/16*     (2006.01)

(52) U.S. Cl.
    CPC ............ *B01D 15/166* (2013.01); *G01N 30/24* (2013.01); *G01N 2030/201* (2013.01); *G01N 2030/326* (2013.01); *G01N 2030/347* (2013.01)

(58) Field of Classification Search
    USPC .......................... 366/152.1, 152.2, DIG. 1–4
    See application file for complete search history.

(56) References Cited

U.S. PATENT DOCUMENTS

| | | |
|---|---|---|
| 4,840,730 A | 6/1989 | Saxena |
| 5,620,524 A * | 4/1997 | Fan ........................... B01J 4/00 118/715 |
| 7,735,878 B2 | 6/2010 | Keene |
| 2002/0196706 A1* | 12/2002 | Kearney ................... B01F 5/06 366/336 |
| 2003/0156952 A1* | 8/2003 | Couillard ............ F04B 11/0075 417/297 |
| 2004/0108273 A1 | 6/2004 | Richardson et al. |
| 2007/0199876 A1 | 8/2007 | Tubby et al. |

OTHER PUBLICATIONS

Kenesis Incorporated, "Vaplock Carboy & Pail Manifolds", kinesishplc.com, 2008 (retrieved on Feb. 22, 2011 from http:www.kinesishplc.com/2008_06_01_archive.html), 4 pages.
International Search Report and Written Opinion in counterpart international application No. PCT/US2011/020792, mailed Mar. 10, 2011; 9 pages.
Extended Search Report in counterpart European patent application No. 11732302.2, mailed on Oct. 6, 2014; 8 pages.

* cited by examiner

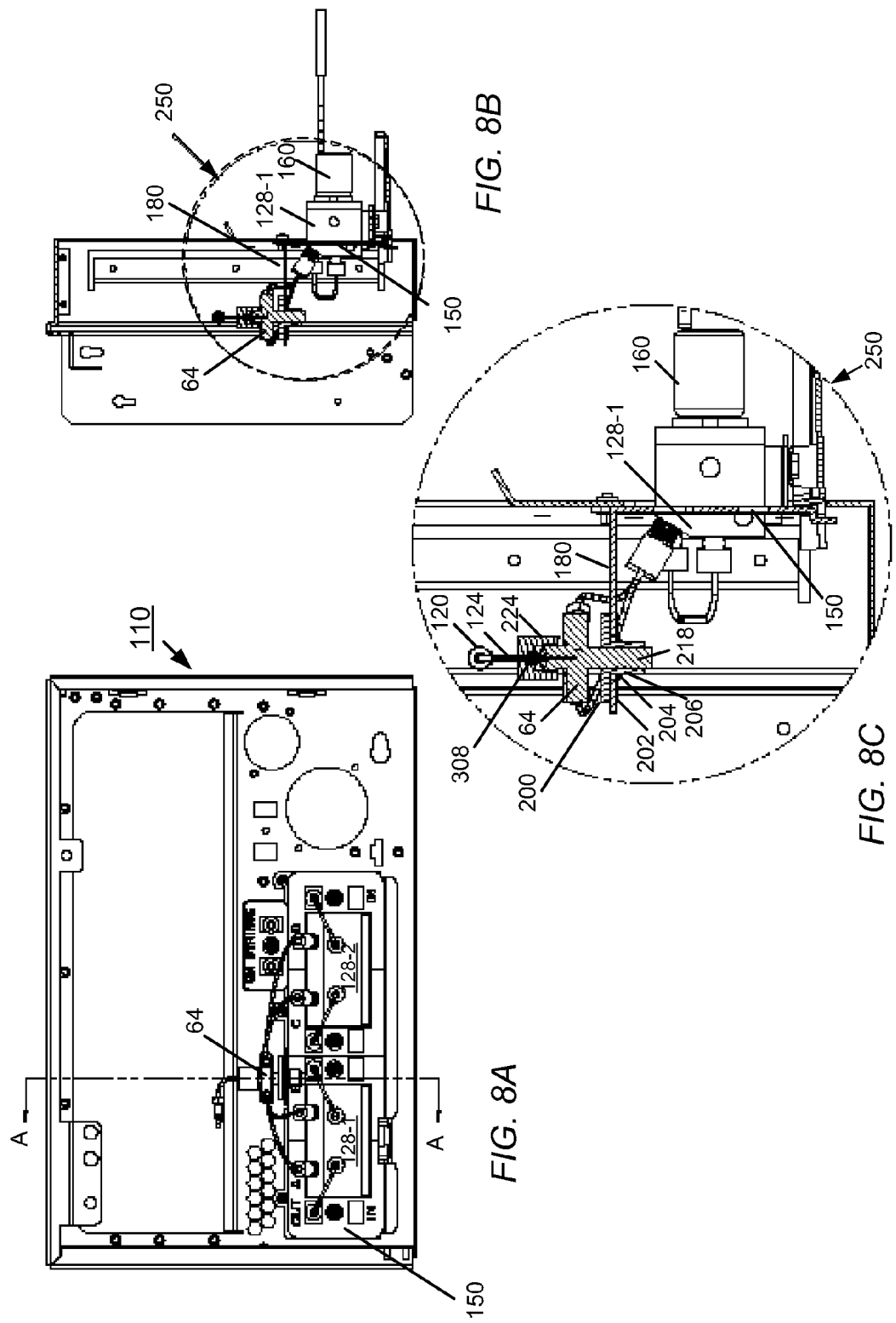

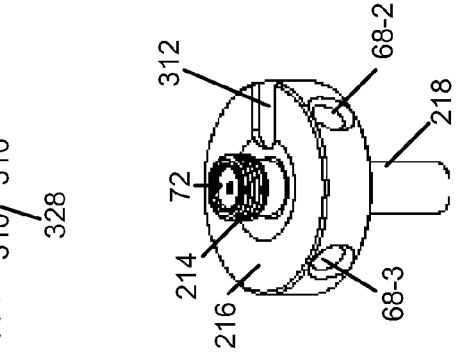
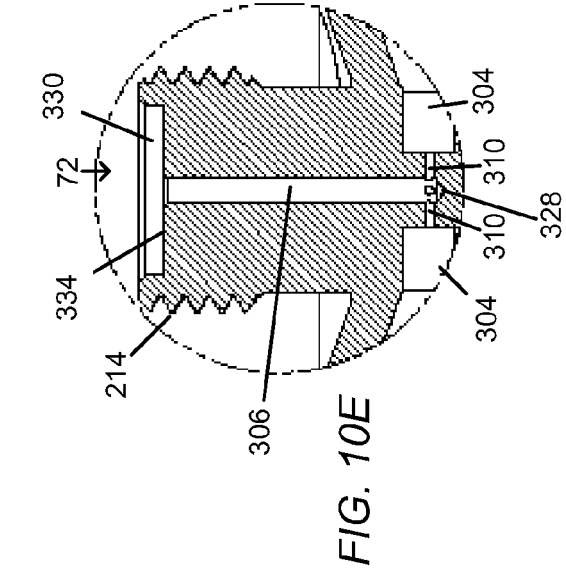
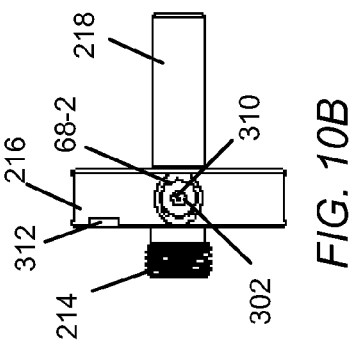
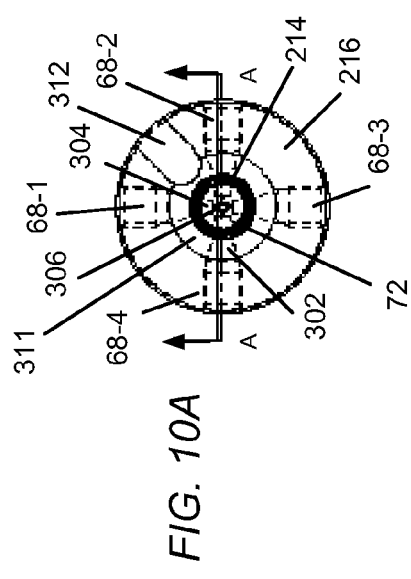
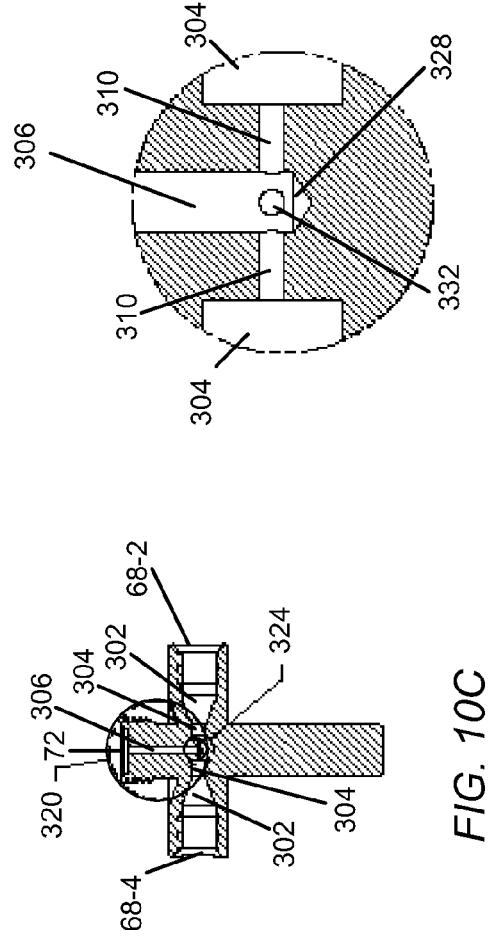

MANIFOLD FOR SOLVENT MIXING IN LIQUID CHROMATOGRAPHY SYSTEMS

RELATED APPLICATION

This application claims priority to and the benefit of U.S. provisional application Ser. No. 61/293,863, filed on Jan. 11, 2010, titled "Liquid Chromatograph Including a Manifold for Low-Pressure Solvent," the entirety of which application is incorporated by reference herein.

FIELD OF THE INVENTION

The invention relates generally to liquid chromatography systems. More specifically, the invention relates to apparatus and methods for low-pressure mixing in liquid chromatography systems.

BACKGROUND

Chromatography is a set of techniques for separating a mixture into its constituents. For instance, in a liquid chromatography application, a pumping system takes in and delivers a mixture of liquid solvents to an autosampler, where an injected sample awaits its arrival. In an isocratic chromatography application, the composition of the liquid solvents remains unchanged, whereas in a gradient chromatography application, the solvent composition varies over time. The mobile phase and the injected sample, which is dissolved in a mixture of solvents, passes to a column, referred to as the stationary phase. By passing the mixture through the column, the various components in the sample separate from each other at different rates and thus elute from the column at different times. A detector receives the separated components from the column and produces an output from which the identity and quantity of the analytes may be determined.

Preferably, the solvent composition (or composition gradient) delivered to the autosampler is a desired, stable composition. Some solvent delivery systems form the desired solvent composition by combining two or more solvents (and/or other fluids) prior to delivery of the composition to the pumping system. Such an arrangement may be referred to as a "low-pressure" gradient system because the mixing occurs on the intake (i.e., low pressure) side of the pumping system.

Before the solvent composition or gradient reaches the injector, however, and thus before injection can take place, a pre-injector dwell volume (also called the gradient delay volume) must first be delivered. In general, the pre-injector dwell volume is the volume of fluid from the point where the solvent composition or gradient forms to the injector valve. Depending upon various factors, such as the use of a mixer, pre-injector dwell volumes can be relatively large (in hundreds of microliters), and, therefore, introduce a sizeable delay to the start of each injection. Historically, however, this delay was insignificant compared to the lengthy chromatographic run times that took tens of minutes and even hours.

This delay becomes problematic, though, when run times are in terms of just a few minutes. For example, if the pre-injector dwell volume is approximately 400 µL, and the pump produces a flow rate of 350 µL per minute, then the time for the gradient to reach the point of injection is over a minute. Thus, the dead time introduced by the pre-injector dwell volume can be a significant percentage of a run, particularly when run times are only minutes in length.

SUMMARY

In one aspect, the invention features a system, comprising a pumping system having a pump and a fluidic inlet port through which fluid is introduced to the pump. A fluid proportioning system is in fluidic communication with the fluidic inlet port of the pumping system to deliver thereto a fluid stream comprised of multiple different fluids. The fluid proportioning system includes a manifold having a plurality of inlet ports, an outlet port connected by tubing to the fluidic inlet port of the pumping system, and an outlet conduit providing an internal fluidic passageway to the outlet port. Each inlet port is fluidically coupled to a fluid source to receive one of the different fluids and to the outlet conduit to deliver thereto the received fluid for delivery out of the manifold through the outlet port to the fluidic inlet port of the pumping system.

In one aspect, the invention features an apparatus for combining fluids comprising a pipe-shaped portion having an outlet port at one end and an internal outlet conduit providing an internal fluidic passageway to the outlet port. A main body has an outer diameter with a plurality of inlet ports for receiving microfluidic tubing. Each inlet port includes an inlet conduit that provides an internal fluidic passageway into the outlet conduit. Each of the plurality of inlet conduits lies in a same plane as every other of the plurality of inlet conduits.

In yet another aspect, the invention features a method of low-pressure mixing of fluids comprising obtaining fluids from a plurality of sources, transporting the fluids in metered fashion into inlet ports of a manifold fluidically coupled on an intake side of a pumping system to an inlet port of the pumping system, delivering the fluids from the inlet ports to an internal outlet conduit of the manifold within which the fluids combine to produce a compositional stream, maintaining the inlet ports in a substantially horizontal orientation to moderate cross-flow of fluids between inlet ports when delivering the fluids to the outlet conduit, and transporting the compositional stream from an outlet port of the manifold into the inlet port of the pumping system.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

FIG. 8A is an exterior view an enclosure panel of the solvent delivery system, with an attached fluidic bracket, installed GPV blocks, and mounted manifold.

FIG. 8B is a cross-sectional side view of the enclosure panel of FIG. 8A.

FIG. 8C is an enlarged view of a region identified in FIG. 8B.

FIG. 10A is a top view of the manifold with four inlet ports.

FIG. 10B is a side view of the manifold.

FIG. 10C is a cross-section side view of the manifold.

FIG. 10D is an enlarged detail view of a region identified in FIG. 10C, which includes the outlet conduit of the manifold.

FIG. 10E is an enlarged detail view of a region identified in FIG. 10C, which includes the outlet port of the manifold.

FIG. 10F is an elevated view of the manifold.

DETAILED DESCRIPTION

Liquid chromatography systems described herein include a solvent delivery system that employs a manifold to combine solvents or fluids received in selected portions from two or more sources. The features of the manifold are particularly suited to low-pressure mixing on an intake side of a pumping unit. To reduce dwell (or delay) volume, the outlet of the manifold is preferably disposed close to an inlet of a pumping unit. In some applications, the manifold does not truly "mix" the two or more solvents, but rather delivers "packets" or "slices" of solvents to the pumping unit, in which actual mixing occurs or begins to occur. In this sense, one may say that the manifold "combines" the solvents, into a stream of packets exiting through an outlet port of the manifold.

Some embodiments of solvent delivery systems introduce the solvents into the manifold preferably in an effectively horizontal plane. As used herein, horizontal preferably means parallel to or in the plane of the horizon and vertical preferably means at right angles to the plane of the horizon. The manifold can be configured to maintain packet integrity, for example, by reducing or minimizing mixing of the solvents at an interface where packets are combined in the manifold. The inlet conduits of the manifold can be maintained in the same horizontal plane, preferably in a symmetrical arrangement, in order to facilitate control of the formation of a desired solvent composition.

Figure 1:
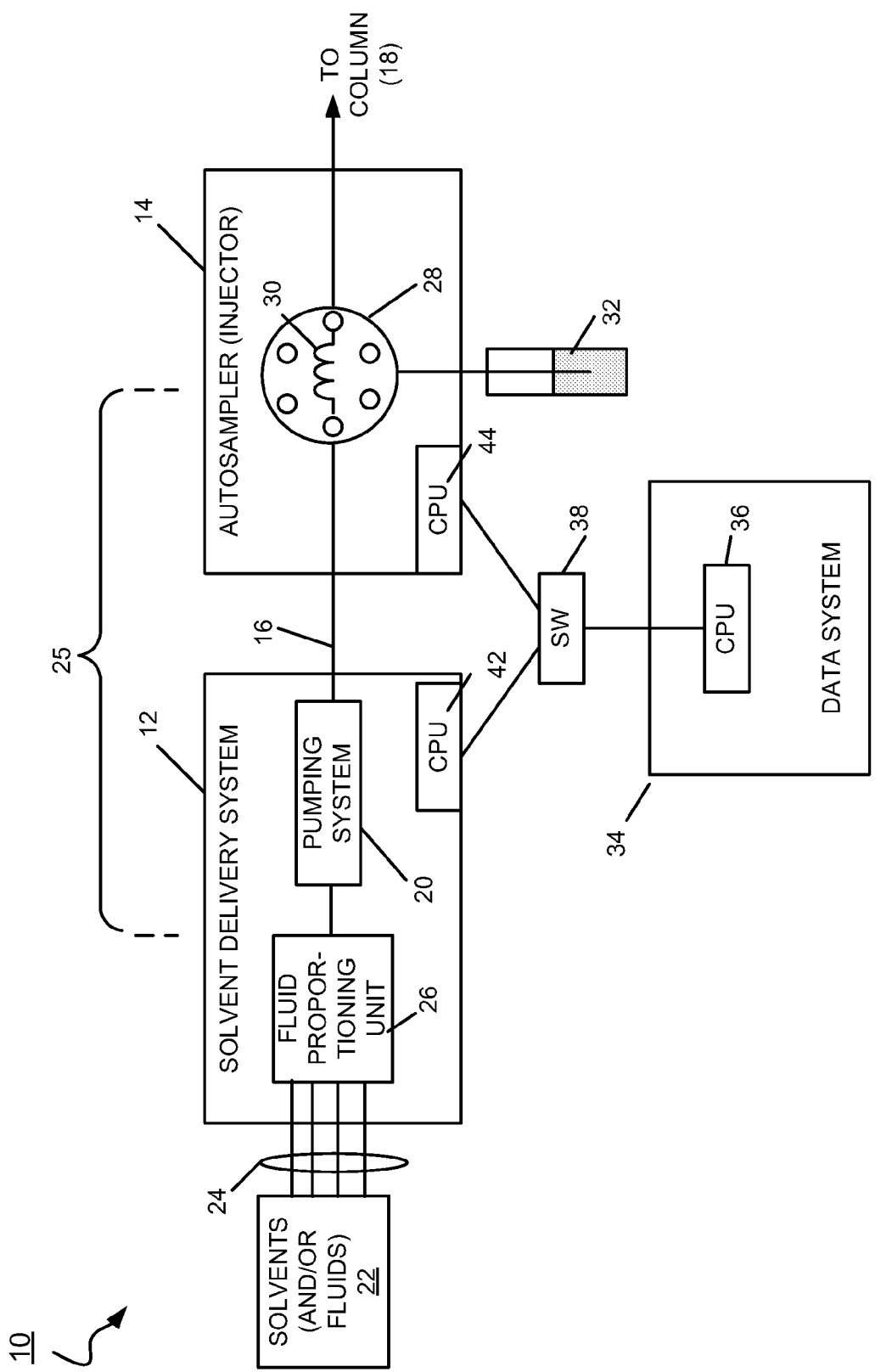
FIG. 1 is a functional block diagram of an embodiment of a liquid chromatography system including a data system, a solvent delivery system, and an autosampler.

FIG. 1 shows an embodiment of a liquid chromatography system 10 for separating a sample into its constituents. The liquid chromatography system 10 includes a solvent delivery system 12 (for example, a QSM or Quaternary Solvent Manager) in fluidic communication with an autosampler 14 (also called an injector or sample manager) through tubing 16. The autosampler 14 is in fluidic communication with a chromatographic column 18. A detector (not shown), for example, a mass spectrometer, is in fluidic communication with the column 18 to receive the output.

The solvent delivery system 12 includes a pumping system 20 in fluidic communication with reservoirs 22 from which the pumping system 20 draws solvents (or fluids) through tubing 24. The pumping system 20 can have a parallel or serial pump configuration. In one embodiment, the pumping system 20 is embodied by a low-pressure mixing gradient pumping system. In the low-pressure mixing gradient pumping system, the combining of solvents begins before the solvents arrive at the pumping system 20. Although described herein primarily with reference to low-pressure mixing gradient pumping systems, other embodiments entail high-pressure mixing gradient pump systems. In contrast to a low-pressure mixing gradient pumping system, in which mixing begins on the intake side of the pumping system 20, the mixing of solvents in a high-pressure mixing gradient pumping system occurs after the solvents pass through the pumping system.

The solvent delivery system 12 has a fluid proportioning unit 26 in fluidic communication with the solvent reservoirs 22 to receive and combine various solvents in metered proportions. This combining of solvents occurs in accordance with an intake profile, and produces a solvent composition that may vary over time. The pumping system 20 is in fluidic communication with the fluid proportioning unit 26 to draw a flow of gradient for delivery to the autosampler 14.

The terms "combining", "mixing" and "mixer", as used herein, are not intended to imply any particular degree of intermingling of the solvents to provide any particular degree of homogeneity of a solvent composition exiting the fluid proportioning unit 26. In some embodiments, the solvent composition exiting the fluid proportioning unit 26 has the form of a series of discrete packets or slices, each packet or slice substantially consisting of one of the four solvents. Mixing to provide a homogeneous solvent of a uniform composition occurs, or occurs in part, in the pumping system 20. Preservation of packet integrity, for example, by the fluid proportioning unit 26 can provide improved control of delivery of a particular solvent composition and/or a particular solvent composition gradient.

Examples of a pumping system that can be modified to implement the pumping system 20 include, but are not limited to, a 2545 Quaternary Gradient Module and a 2555 Quaternary Gradient Module, manufactured by Waters Corp. of Milford, Mass.

The autosampler 14 includes an injector valve 28 having a sample loop 30. The autosampler 14 operates in one of two states: a load state and an injection state. In the load state, the position of the injector valve 28 is such that the autosampler 14 loads the sample 32 into the sample loop 30; in the injection state, the position of the injector valve 28 changes so that autosampler 14 introduces the sample in the sample loop 30 into the continuously flowing mobile phase from the solvent delivery system 12. The mobile phase thus carries the sample into the column 18. The pre-injection dwell volume 25 of this embodiment of chromatography system 10 extends from where the gradient forms within the fluid proportioning unit 26 on the intake side of the pumping system 20 to the injector valve 28 of the autosampler 14.

The chromatography system 10 further includes a switch 38 (e.g., an Ethernet switch) that is in signal communication with a processor 42 of the solvent delivery system 12 and a processor 44 of the autosampler 14. A data system 34 has a processor 36 that is in communication with the switch 38 for handling signal communication between the solvent delivery system 12 and the autosampler 14. Signal communication among the various systems and instruments can be electrical or optical, using wireless or wired transmission.

Through the data system 34, a user can download various parameters and profiles (e.g., a gradient profile). The downloaded parameters include method parameters for the solvent delivery system 12 and the autosampler 14 and injection parameters for the autosampler 14. Method parameters for the solvent delivery system 12 include, but are not limited to, a user-settable pre-injection (dwell) volume parameter and an initial flow rate parameter. Downloaded injection parameters include, but are not limited to, sample vial location and sample volume. The processor 42 of the solvent delivery system 12 controls the flow rate of the pumping system 20 and the gradient formation in accordance with downloaded method parameters. The processor 44 of the autosampler 14 controls the loading and injection stages of operation in accordance with downloaded method and injection parameters.

Figure 2:
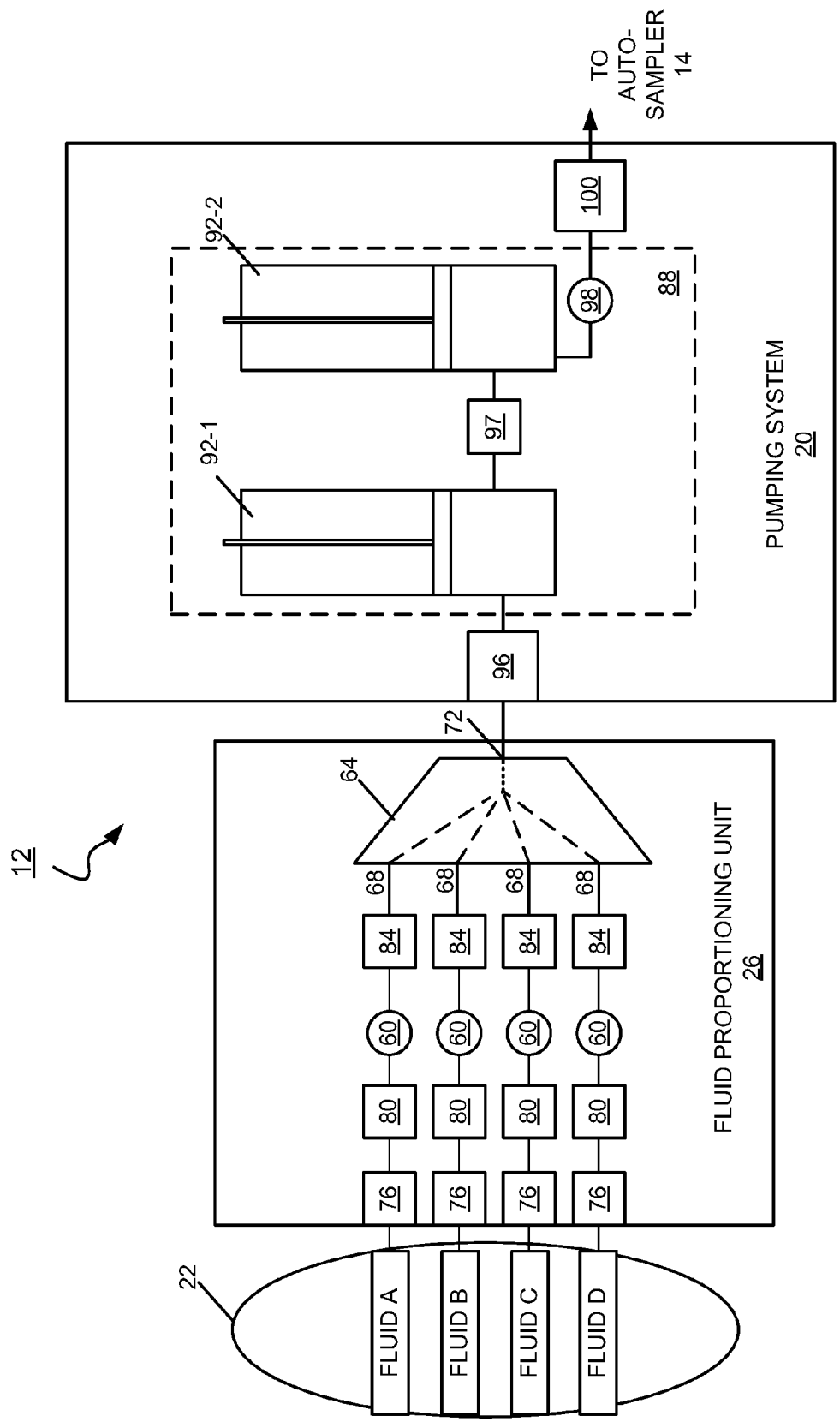
FIG. 2 is a schematic diagram of an embodiment of the solvent delivery system including a fluid proportioning unit and a pumping system, and the fluid proportioning unit having a manifold.

FIG. 2 shows an embodiment of the solvent delivery system 12 including the fluid proportioning unit 26 in fluidic communication with the pumping system 20. The following description is particularly directed to combining fluids arriving from four fluid sources. One of ordinary skill will recognize that principles described herein are optionally applied to other fluids and to less than or more than four fluids sources.

The fluid proportioning unit 26 includes four gradient proportioning valves (GPV) 60 fluidically connected to a manifold 64 (schematically represented as a multiplexer) having four inlet ports 68 and one outlet port 72. Lines from four sources 22 of solvents, or other fluids, extend through filters 76 prior to passing through degassers 80 and arriving at the GPVs 60. Through filters 84, the output of each GPV 60 passes to one of the inlet ports 68 of the manifold 64.

The pumping system 20 includes a pump unit 88 with two pumps, a primary pump 92-1 and an accumulator pump 92-2, fluidically connected in series. Alternatively, the pumping system 20 can have a parallel pump configuration. In one embodiment, the pumping system 20 can provide a flow rate in the range of 0.010 ml/min to 2 ml/min up to 15,000 psi. Connected to the primary pump 92-1 is an inlet check valve 96. The inlet check valve 96 is fluidically connected to an outlet port 72 of the manifold 64, to receive a consistent stream of solvent packets, with relatively little dispersion of solvents at interfaces between packets, from the manifold 64 for delivery to the pump unit 88. An outlet of the primary pump 92-1 is coupled to an inlet of the accumulator pump 92-2 through an outlet check valve 97. An outlet of the accumulator pump 92-2 is fluidically connected to a vent valve 98. A mixer/filter 100 fluidically coupled downstream of the vent valve 98 provides additional filtering and mixing prior to arrival of the solvent composition at, for example, the autosampler 14 (FIG. 1).

Figure 3:
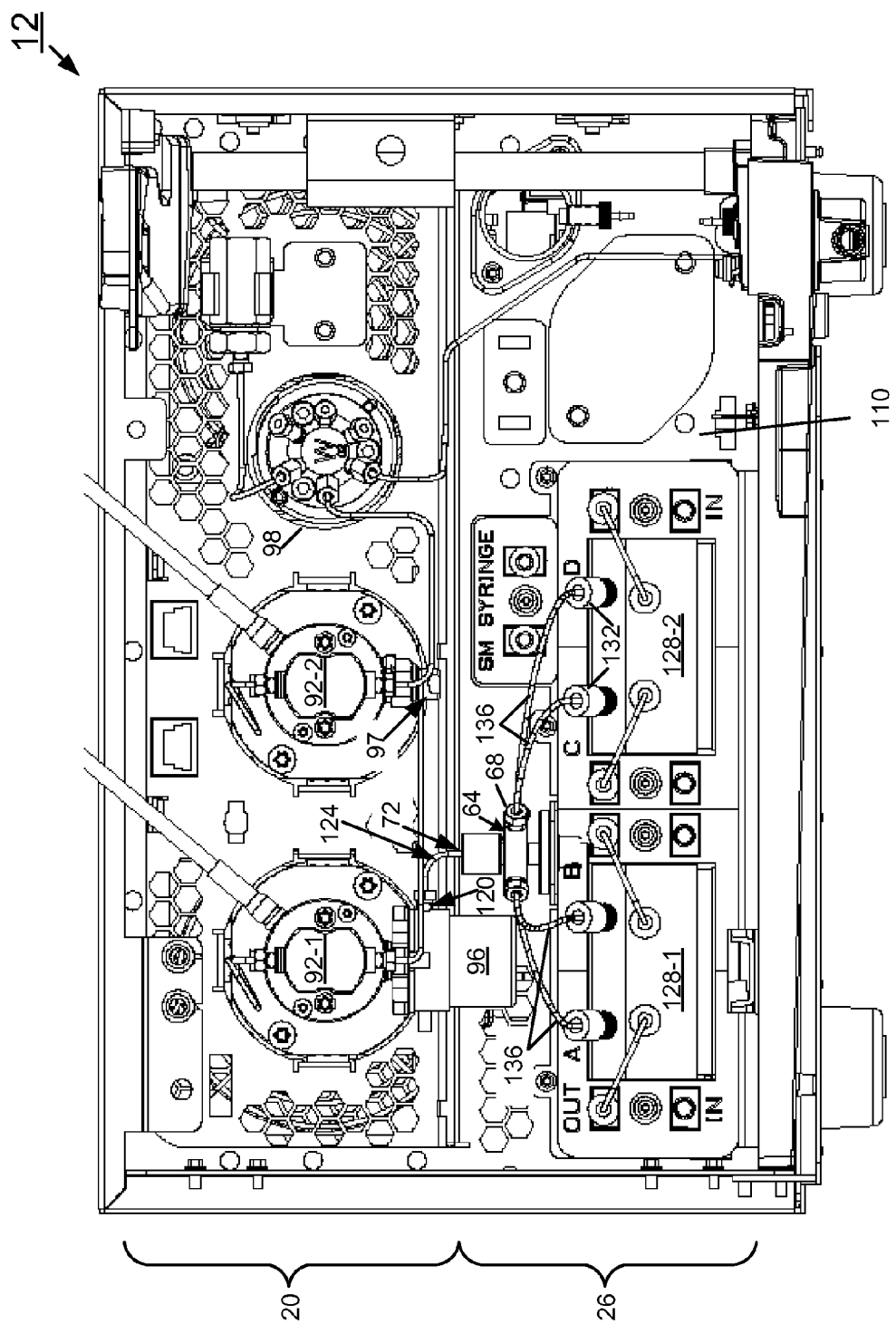
FIG. 3 is an exterior view of one embodiment of the solvent delivery system with the pumping system installed above the fluid proportioning unit.

FIG. 3 shows an exterior view of one embodiment of the solvent delivery system 12. The exterior view shows a metallic bulkhead 110, behind which is the pumping system 20, with its primary and accumulator pumps 92-1, 92-2, disposed adjacent to and above the fluid proportioning unit 26. An outlet of the primary pump 92-1 is plumbed to an inlet of the accumulator pump 92-2, and an outlet of the accumulator pump 92-2 is plumbed to the vent valve 98. The inlet check valve 96 is fluidically connected to the inlet of the primary pump 92-1.

The manifold 64 is situated adjacent to one side of the inlet check valve 96. The outlet port 72 of the manifold 64 is fluidically connected to an inlet port 120 of the inlet check valve 96 by a short tube 124. The length of this tube 124 contributes to the delay volume of the chromatography system. Accordingly, the closer the manifold 64 is disposed to the inlet check valve 96, the lesser the delay volume. In one embodiment, the length of the tube 124 is less than approximately 2 inches.

In this embodiment, the fluid proportioning unit 26 has two GPV blocks 128-1, 128-2 (generally, 128), each supporting two GPVs 60 (not visible). Other embodiments can have a single block supporting four GPV valves or four individual blocks each supporting one GPV valve. Each of the GPVs is plumbed to one of the inlet ports 68 of the manifold 64, as described in more detail below.

Figure 4:
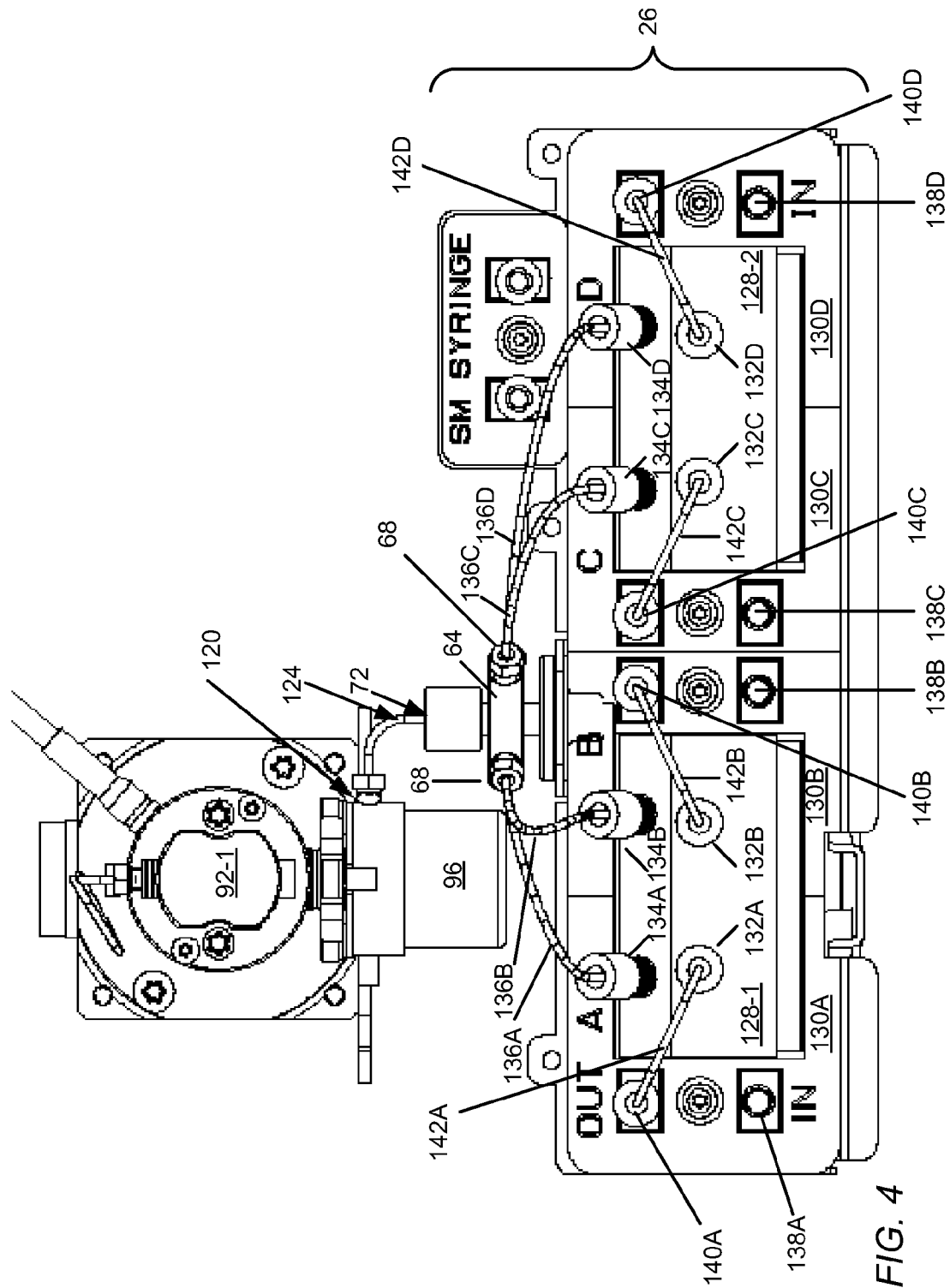
FIG. 4 is the exterior view of FIG. 3 showing in closer detail the fluid proportioning unit and a primary pump of the pumping system.

FIG. 4 shows the exterior view of FIG. 3, specifically isolated to the fluid proportioning unit 26 and the primary pump 92-1 of the pump unit 88. The fluid proportioning unit 26 has four vertically oriented partitions 130, here labeled A, B, C, and D. Each partition 130 corresponds to one of the solvents (referred to herein as Solvent A, Solvent B, Solvent C, and Solvent D). (Herein, the letter following a reference numeral corresponds to the particular solvent, A-D, with which that partition, port, etc. is associated). Partitions 130A and 130B share the GPV block 128-1, and partitions 130C and 130D share the GPV block 128-2. In each partition 130, there is one inlet port 132 disposed vertically below one outlet port 134; accordingly, each GPV block 128, which is shared by two partitions, has two inlet ports 132 and two outlet ports 134. Tubing 136 connects each outlet port 134 to one of the inlet ports 68 of the manifold 64. (Only two of the inlet ports 68 of the manifold 64 are visible, the view of the other two inlet ports being blocked).

Each partition 130 also has a degasser inlet port 138 disposed vertically below a degasser outlet port 140. The degasser inlet and outlet ports 138, 140 of partitions 130A and 130B are disposed on opposite sides of the GPV block 128-1, and the degasser inlet and outlet ports 138, 140 of partitions 130C and 130D are disposed on opposite sides of the GPV block 128-2, wherein the degasser inlet and outlet ports 138, 140 of partitions 130B and 130C are disposed between the GPV blocks 128.

Tubing 142 fluidically connects the outlet port 140A for the partition 130A to the inlet port 132A of the GPV block 128-1; a tube 142 fluidically connects the outlet port 140B for the partition 130B to the inlet port 132B of the GPV block 128-1. Similarly, the outlet port 140C for the partition 130C is fluidically connected by a tube 142 to the inlet port 132C of the GPV block 128-2; and the outlet port 140D for the partition 130D is fluidically connected by a tube 142 to the inlet port 132D of the GPV block 128-2. Each of the outlet ports 134 of the GPV blocks 128 is fluidically connected to one of the inlet ports 68 of the manifold 64 by a tube 136.

Figure 5:
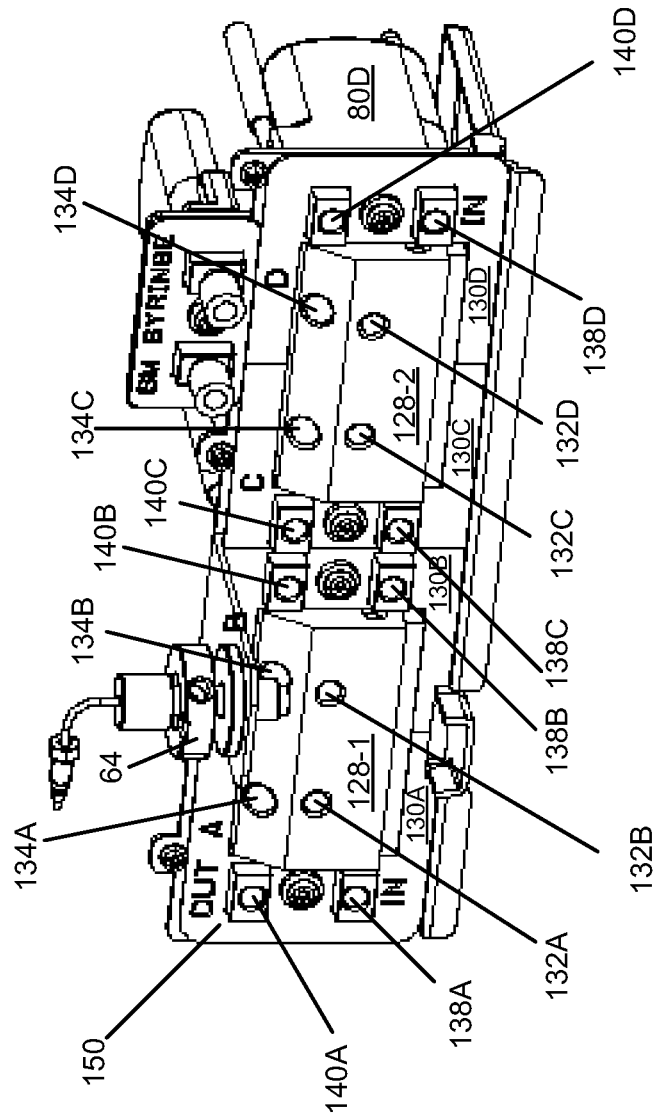
FIG. 5 is an isometric external view of the fluid proportioning unit.

FIG. 5 shows an isometric view of the fluid proportioning unit 26 of FIG. 4 without the tubing 136, 142, pump 92-1, and inlet check valve 96 to simplify the illustration. The isometric view shows a degasser 80D (see also FIG. 2) disposed on a reverse side of a fluidic bracket 150 directly behind partition 130D. The degasser inlet and outlet ports 138D, 140D connect to this degasser 80D. Although not seen, there is a separate degasser on the reverse side of the fluidic bracket 150 for each of the other partitions 130A, 130B, 130C.

Figure 6:
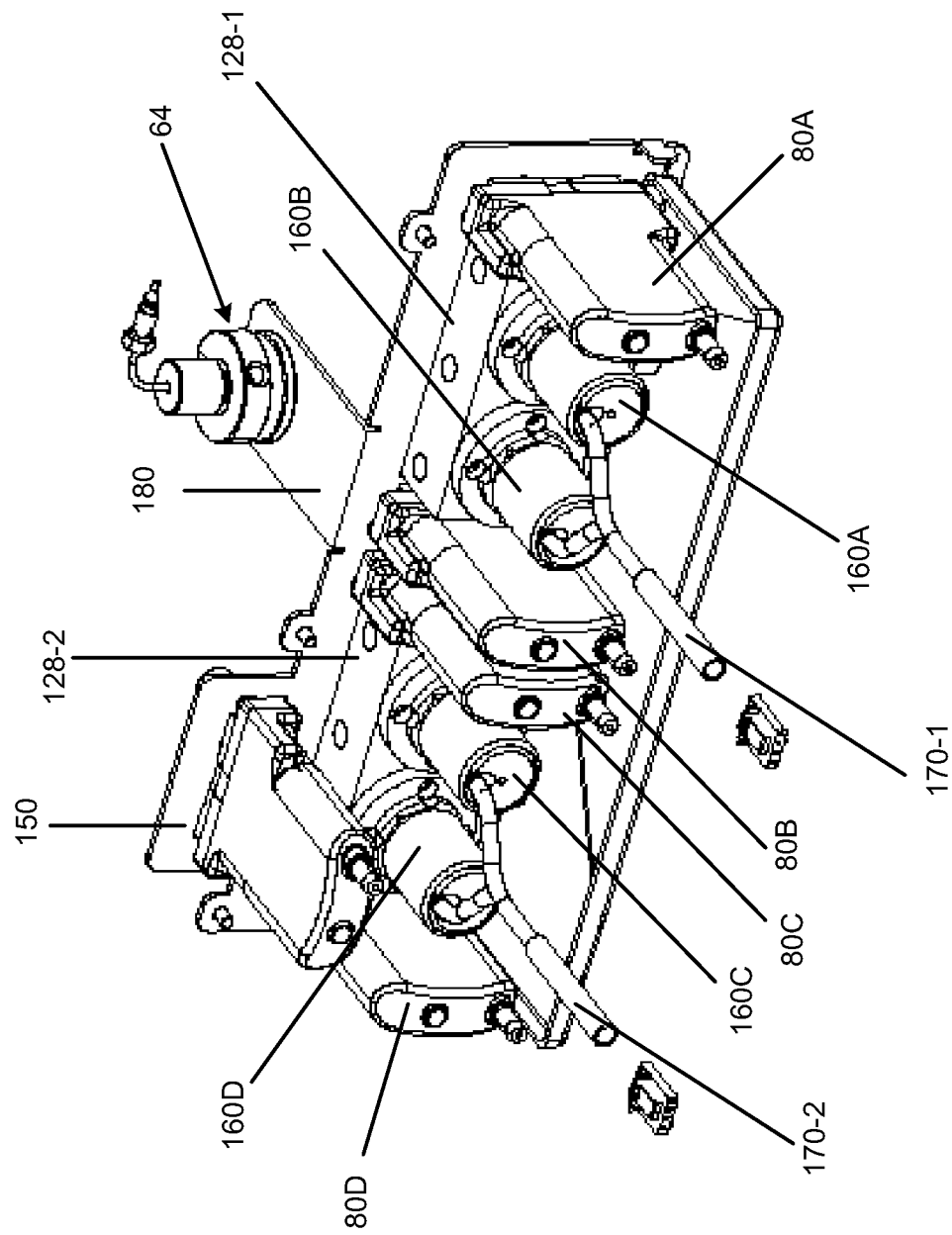
FIG. 6 is an isometric view of the fluid proportioning unit from a reverse side.

FIG. 6 is an isometric view of the fluid proportioning unit 12 from the reverse side of the fluidic bracket 150 to show a degasser 80 for each of the solvents and a solenoid 160 for operating each of the GPVs 60. Solenoids 160A and 160B control the operation of GPVs coupled to GPV block 128-1, whereas solenoids 160C and 160D control the operation of GPVs coupled to GPV block 128-2. Electrical power cords 170-1, 170-2 carry power to the solenoids 160: the electrical power cord 170-1 forks to carry power to solenoids 160A and 160B; and the electrical power cord 170-2 forks to carry power to solenoids 160C and 160D.

Extending orthogonally from a top edge of the fluidic bracket 150 is a manifold bracket 180 that is part of a manifold mounting assembly, described in connection with FIG. 7.

Figure 7:
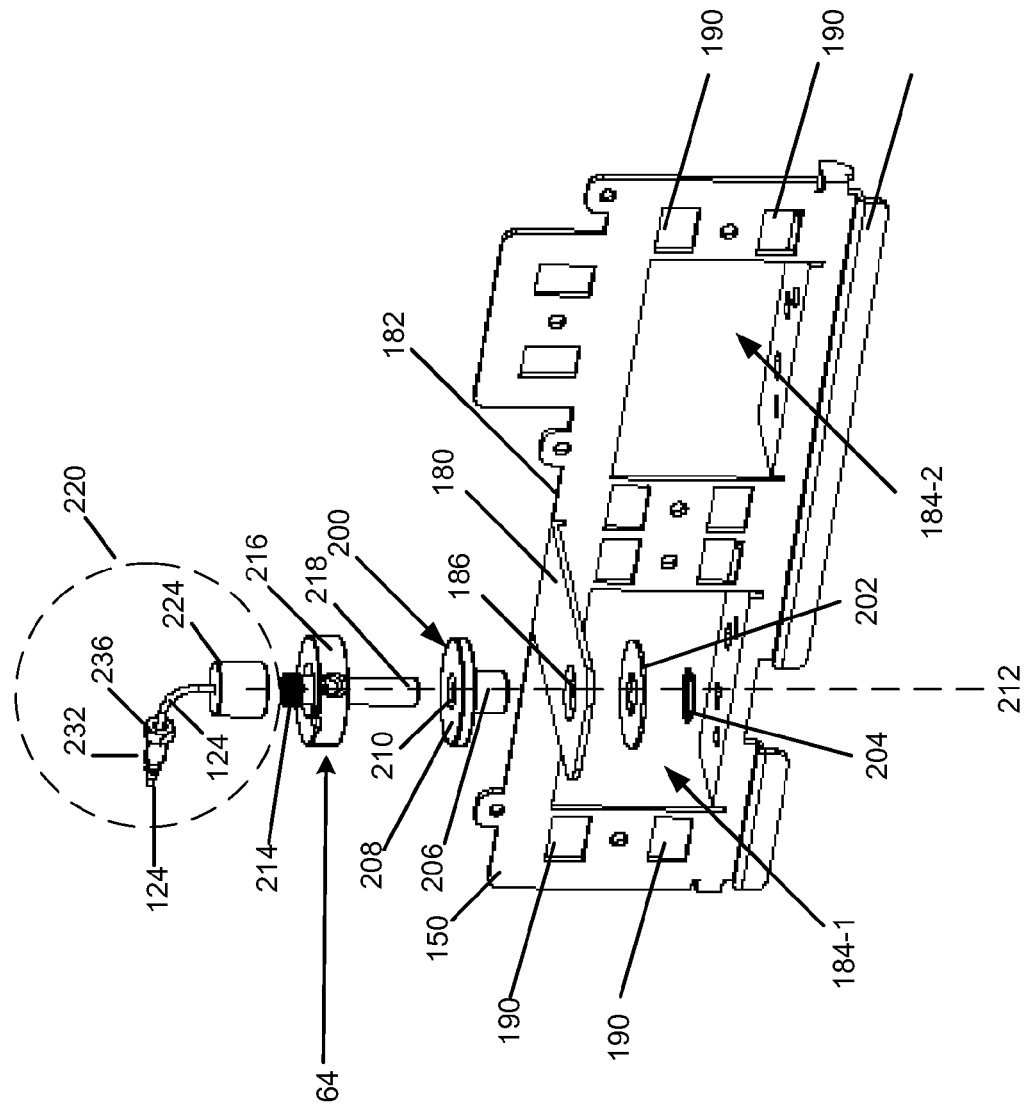
FIG. 7 is an isometric view of a fluidic bracket used in the fluid proportioning unit to hold the GPV (gradient proportioning valve) blocks, degassers, and manifold.

FIG. 7 shows an embodiment of the fluidic bracket 150 used in the fluid proportioning unit 26 to hold the GPV blocks 128 (FIG. 3) and the manifold 64 (FIG. 6). The fluidic bracket 150 includes a pair of bays 184-1, 184-2 (generally, 184). Each bay 184 closely receives one of the GPV blocks 128. The manifold bracket 180 extends substantially orthogonally from an exterior face of the fluidic bracket 150 near a top edge 182 of the fluidic bracket 150. The manifold bracket 180 has an opening 186 near the end that is distal from the exterior face of the fluidic bracket. The fluidic bracket 150 has several cutout windows 190 through which to access the degasser inlet and outlet ports 138, 140 (FIG. 4).

Also shown is an exploded view of the components of the manifold mounting assembly, including a bushing 200, a washer 202, and a push nut 204. The bushing 200 has a cylindrical post portion 206, cylindrical planar portion 208, and a bore 210 that extends fully through the two portions. The post portion 206 of the bushing 200 sits in the opening 186 of the manifold bracket 180, entering the opening 186 from above: the diameter of the cylindrical post portion 206 is smaller than the diameter of the opening 186 in the manifold bracket 180, such that the post portion 206 fits loosely in the manifold bracket opening 186; and the diameter of the cylindrical planar portion 208 is greater than that of the manifold bracket opening 186, such that a lower surface of the planar portion 208 sits flush atop the top surface of the manifold bracket 180 and always covers the opening 186 irrespective of how much the bushing 200 moves.

From below the manifold bracket 180, the washer 202 slips over the post portion 206. Similar to the planar portion 208, the size of the washer 202 is such that the washer 202 always covers the opposite side of the manifold bracket opening 186 irrespective of how much the bushing 200 moves. The push nut 204 follows the washer 202 and secures to the post portion 206 of the bushing 200, while urging the washer 202 flush against the underside of the manifold bracket 180. The bushing 200 sits movably within the manifold bracket opening 186, wherein the bushing is capable of rotating and of slight movement in any direction within a horizontal plane. The push nut 204 secured below the manifold bracket 180 substantially restricts any vertical movement of the bushing 200. The size of the cylindrical planar portion 208 and washer 202 resists any tilting of the bushing 200.

The manifold 64 has a wheel-shaped main body 216, a cylindrical threaded upper portion 214, and a cylindrical lower extension 218. Although described as separate features, in one embodiment, the main body 216, upper portion 214, and lower extension 218 are inseparable integral features of the manifold 64. In other embodiments, the main body 216, upper portion 214, and lower extension 218 are separate components joined together to produce the manifold. The manifold 64 is preferably made of stainless steel.

The wheel-shaped main body 216 has a circular frame and an imaginary central axis 212 extending orthogonally through the hub of the main body 216. The upper portion 214 and lower extension 218 extend along this central axis 212 and, from opposite sides of the main body 216, meet at the main body's center, thus looking like an axle passing through the central hub of a wheel.

The outer diameter of the cylindrical lower extension 218 is slightly smaller than the inner diameter of the bushing bore 210, such that the lower extension 218 can slide freely into and out of the bore 210, a feature particularly advantageous when connecting the manifold 64 to the inlet check valve 96 of the pumping system 20. (An outer diameter preferably refers to an exterior surface of a cylindrical feature; whereas an inner diameter preferably refers to an interior surface of a cylindrical feature.)

When mounted to the manifold bracket 180 as preferred, the threaded upper portion 214 and lower extension 218 of the manifold 64 preferably stand upright in a substantially vertical orientation, with the wheel-shaped main body 210 being generally horizontally disposed.

In addition, the various components 200, 202, and 204 attach the manifold 64 to the manifold bracket 180 in a manner that optionally permits some up and down (preferably vertical) motion within the bore 210 of the bushing, some side-to-side horizontal motion of the bushing itself within the manifold bracket opening 186, but substantially no tilting motion of the manifold, that is, for example, to tilt about a horizontal axis. Lateral movement of the manifold 64 is, for example, approximately 1/8". The range of movement provided by the manifold mounting assembly accommodates, for example, mechanical tolerances. In addition, requiring the solvent delivery system 12 to be level, for example, preferably within 1 or 2 degrees of level, produces a desired vertical orientation of the upper portion 214 and lower extension 216 of the manifold 64 and desired horizontal orientation of main body 210 of the manifold 64.

An outlet connector assembly 220 (also referred to as fittings 220), for fluidically connecting the manifold 64 to the inlet check valve 96 of the pumping system 20, includes a cap 224, the outlet tube 124 (FIG. 3) extending from the cap, a ferrule 232 for closely entering an inlet port 120 (FIG. 3) of the inlet check valve 96, and a nut 236 for urging the ferrule tightly into that inlet port. The tube 124 extends fully through the ferrule 232, with a small portion of the tube 124 extending therefrom. The cap 224 has a central opening (not shown), providing a passageway into the tube 124 for fluid coming from the manifold 64, and a threaded interior for mating with the threaded upper portion 214 of the manifold 64.

The freedom of movement of the lower extension 218 of the manifold with the manifold bracket bore 210 permits an assembler to raise or lower the manifold, as needed, to a precise point where the ferrule 232 of the connector assembly 220 can reach, enter, and be secured to the inlet port 120 of the inlet check valve 96. This freedom of movement additionally facilitates removal of the inlet check valve 96 (FIG. 6), as illustrated in more detail below.

Other configurations of the manifold bracket, bushing, and/or manifold extension fall within the scope of the principles provided herein. As examples, rather than extending from near the center of the top edge 182 of the fluidic bracket 150, the manifold bracket 180 can alternatively extend from any externally facing surface of the fluidic bracket 150, such as from the bottom edge or from a side region, taking into consideration the tubing and a desired amount of separation of the manifold from the inlet check valve. As another example, the manifold 64 can be disposed behind the bulkhead 110.

FIG. 8A shows an exterior view of the bulkhead 110 of the solvent delivery system 12, with an attached fluidic bracket 150, installed GPV blocks 128, and mounted manifold 64. Cross-sectional line (A-A) runs substantially along the central axis 212 (FIG. 7) of the manifold 64.

FIG. 8B shows a side view of the bulkhead 110 in accordance with the cross-section A-A of FIG. 8A, including a T-shaped cross-section of the manifold 64 sitting in a bushing 200 on the surface of the manifold bracket 180 of the fluidic bracket 150. On the reverse side of the fluidic bracket 150 is a side view of one of the GPV blocks 128 and a solenoid 160. A circle 250 surrounds a section to be shown in closer detail in FIG. 8C.

In FIG. 8C, the bushing 200 sits atop the manifold bracket 180 flush against the manifold bracket's top surface, the post portion 206 of the bushing 200 extending through the opening in the manifold bracket 180. The push nut 204 and the washer 202 on the underside of the manifold bracket 180 couples tightly to the post portion 206. This coupling operates to keep the bushing 200 from coming out of the manifold bracket opening 186, while permitting the bushing some movement in its horizontal plane. The lower extension 218 of the manifold 64 sits freely within the bore 210 of the bushing 200. A portion of the lower extension 218 can be seen to extend beyond the lowest extent of the post portion 206 of the bushing 200. In this orientation, the manifold 64 has little or no ability to tilt (about a horizontal axis), but can rotate about a vertical axis and translate in the vertical and horizontal planes. Such translation optionally eases, for example, connection and disconnection of the outlet tube 124 and fitting from the inlet check valve 96. The cap 224 is tightly secured to the threaded upper portion 214 of the manifold, thereby securing a tight fit between a ferrule 308 and an internal outlet conduit 306 (FIG. 10C) of the manifold.

Figure 9A:
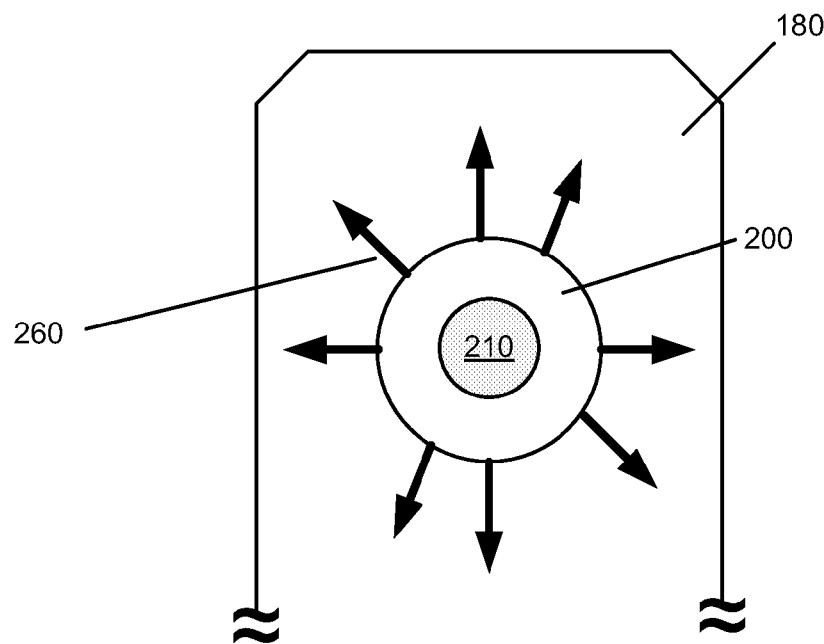
FIG. 9A is a top view of a bushing sitting within an opening in a manifold bracket of the fluidic bracket.

FIG. 9A shows the bushing 200 sitting within the manifold bracket opening. Arrows 260 show generally the direction of horizontal movement permitted by the dimensions of the inner diameter of the manifold bracket opening and the outer diameter of the post portion 206 of the bushing.

Figure 9B:
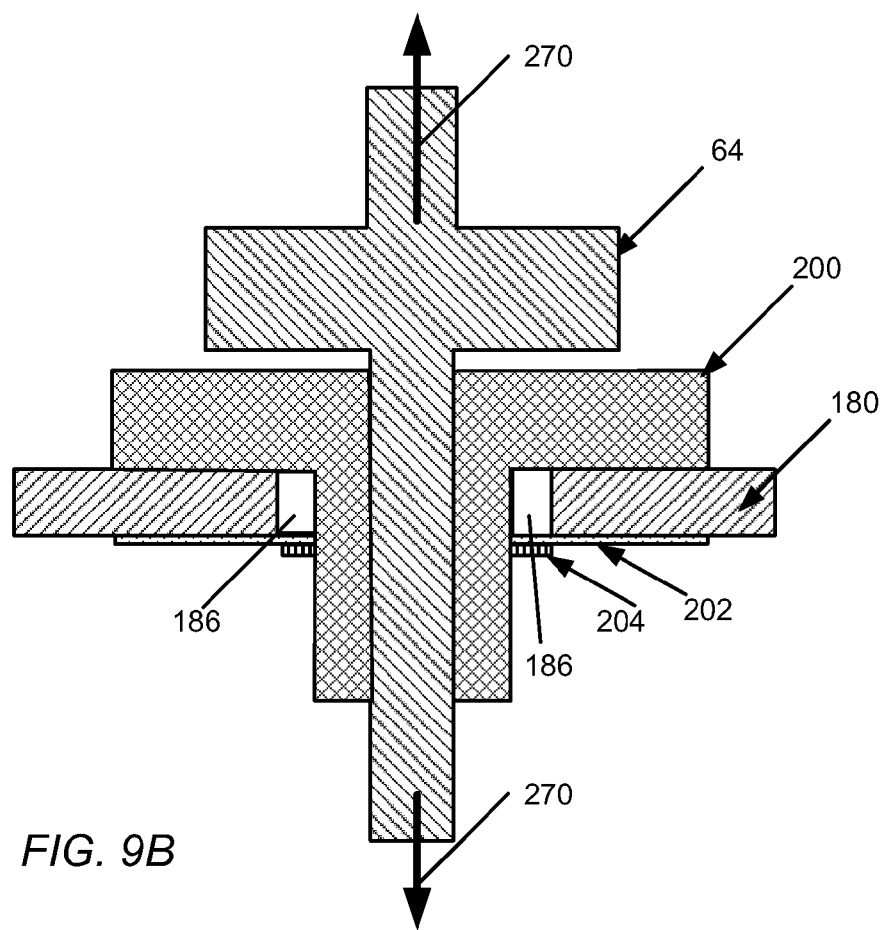
FIG. 9B is a side view of the manifold with its lower extension disposed within a bore of the bushing.

FIG. 9B shows a side view of the manifold 64 with its lower extension 218 disposed within the bore of the bushing 200. Arrows 270 show generally the direction of vertical movement permitted by the dimensions of the inner diameter of the bushing bore and the outer diameter of the lower extension 218 of the manifold 64.

FIG. 10A shows a top view of the manifold 64 with four inlet ports 68-1, 68-2, 68-3, 68-4 (generally, 68), which mate with tube fittings of the four tubes 136 (FIG. 4). Shown in phantom, the inlet ports 68 are internal to the manifold. Preferably, the inlet ports 68 are symmetrically distributed about the hub of the wheel-shaped main body 216 and lie in the same plane. (When mounted to the fluidic bracket, the manifold mounting assembly maintains the co-planar inlet conduits in a horizontal plane, within a tilt angular range of, for example, 1 to 2 degrees. Beneficially, the horizontal orientation and symmetrical distribution of the inlet ports reduce retention time variations and the cross-flow of solvents between inlet conduits, particularly when producing a packet stream comprised of multiple solvents and solvents of different densities. Greater variability of the packet stream can occur without control of the manifold orientation, and/or without symmetrical distribution of conduits in the manifold than with such control and/or distribution.) Each inlet port 68 is a tube receptacle with a conical region 302 that tapers to a tip 304 having a narrower inner diameter than the inlet port 68. The top view provides a view into the outlet port 72 of the manifold 64, showing the tip 304 of each inlet port 68. Each tip 304 approaches and connects to an outlet conduit 306 at the center of the outlet port 72 (the outlet conduit comes out of the plane of the page, being orthogonal to the plane of the inlet ports 68 and tips 304). A solvent tube enters each inlet port 68 and extends to the end of the tip 304.

The connection between each tip 304 and the outlet conduit is made through a relatively short inlet conduit 310 (FIG. 10D). The inner diameter of the outlet conduit 306 is preferably wider than the inner diameters of the inlet conduits 310. A recess in a surface of the wheel-shaped main body 216, a moat 311 encircles the upper portion 214 of the manifold, which may collect fluid escaping and dripping down the manifold, for example, when the inlet check valve 96 (FIG. 2) is detached. Between inlet ports 68-1 and 68-2 is a recess 312, which provides as a drain for any fluid that collects in the moat 311. Cross-sectional line (A-A) cuts the manifold 64 in half, passing through inlet ports 68-2 and 68-4.

FIG. 10B shows a side view of the manifold 64 including the upper portion 214 having a threaded outer diameter, the wheel-shaped housing 216, and the lower extension 218. The side view of the inlet port 68-2 shows three concentric bores corresponding to the successively narrowing passageways of the inlet port 68-2, tip 304 and inlet conduit 310 leading to the outlet conduit 306.

FIG. 10C shows a side view of the manifold 64 in accordance with the cross-section A-A of FIG. 10A. As shown, the inlet ports 68-2, 68-4 taper to tips 304 that approach the outlet conduit 306. The outlet conduit 306 extends to the mouth of the outlet port 72. Although shown to be a linear conduit, other embodiments of the outlet conduit 306 can be serpentine. Not shown are the inlet conduits between the tips 304 and outlet conduit. Two circles 320, 324 surround regions selected for zoomed-in views corresponding to FIGS. 10D and 10E, respectively.

FIG. 10D shows a detail view of the region surrounded by the circle 324 in FIG. 10C. One end 328 of the outlet conduit 306 is closed. Near this closed end 328 are openings 332 into the outlet conduit 306. The inlet conduits 310 of the inlet ports 68 meet the outlet conduit 306 at these openings 332 (only three of which are shown, the fourth being on the unseen side of the outlet conduit), thus providing a fluidic passageway from the inlet port 68 into the outlet conduit 306. The inner diameters of the inlet conduits 310 are preferably narrower than the inner diameters of the solvent tubes. When tube fittings, such as a ferrule and nut, hold a solvent tube in place within an inlet port 68, the end face of the solvent tube contacts the end face of the tip 304 and the inner diameters of the solvent tubes align with the inner diameter of the inlet conduits 310.

The point where the fluids enter the outlet conduit 306 from the inlet ports 68 can be considered the mixing point, that is, the point where different fluids arriving from different sources first combine and begin to mix, albeit not homogeneously. Further, maintaining the inlet ports preferably in a substantially horizontal orientation moderates the cross-flow of fluids between inlet ports as the inlet conduits 310 deliver the fluids to the outlet conduit through the openings 332. Any tilt in the manifold would result in a downward or upward flow of fluid into the one or more inlet conduits at the low or high end of the tilt.

FIG. 10E shows a detail view of the region surrounded by the circle 320 in FIG. 10C. The region includes the threaded outer diameter 214 of the outlet port 72. The outlet conduit 306 extends from the closed end 328 near the inlet conduits 310 to the mouth 330 of the outlet port 72. At the bottom of the mouth is a flat surface 334 against which the ferrule 308 (FIG. 8C) and tubing 124 press when the cap 224 is secured to the threaded upper portion 214 of the manifold 64, as illustrated further detail in FIG. 11B and FIG. 11C.

FIG. 10F shows an elevated view of the manifold 64 including the threaded outer diameter of the upper portion 214, the wheel-shaped housing 216, and the lower extension 218. Also shown are two inlet ports 68-2, 68-3 of the four inlet ports and the depression 312.

Figure 11A:
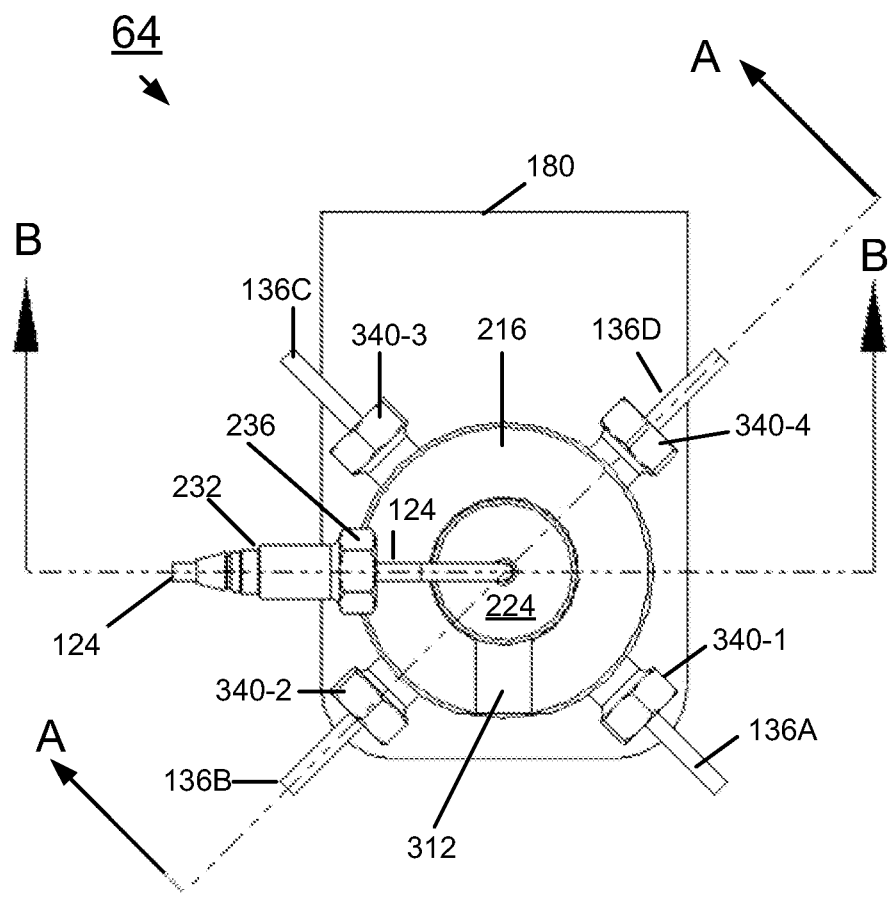
FIG. 11A is a top view of the manifold.

FIG. 11A shows another top view of the manifold 64, here shown with an attached outlet connector assembly 220 (FIG. 7) comprised of the cap 224, tubing 124, ferrule 232, and nut 236. Connected to each of the inlet ports 68-1, 68-2, 68-3, and 68-4 (FIG. 10A) is a respective tube fitting 340-1, 340-2, 340-3, 340-4. Each tube fitting 340 fluidically connects tubing 136 to one of the outlet ports 134 of the GPV blocks 128 (FIG. 4). Cross-sectional line (A-A) passes through the center of the manifold 64 and through tube fittings 340-2, 340-4. Cross-sectional line (B-B) passes through the center of manifold 64 and through the tubing 124, ferrule 232, and nut 236 of the outlet connector assembly.

Figure 11B:
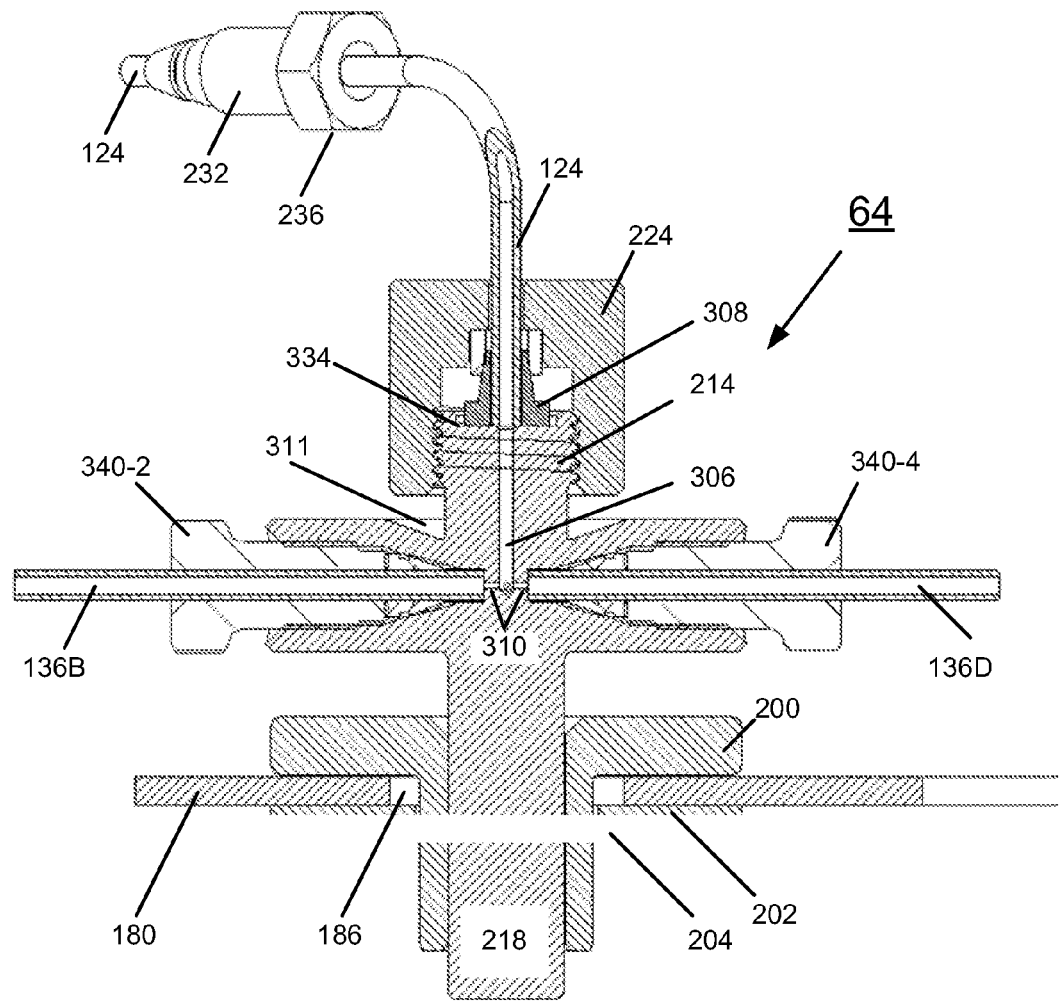
FIG. 11B shows a side view of the manifold in accordance with a cross-section taken along line A-A in FIG. 11A.
Figure 11C:
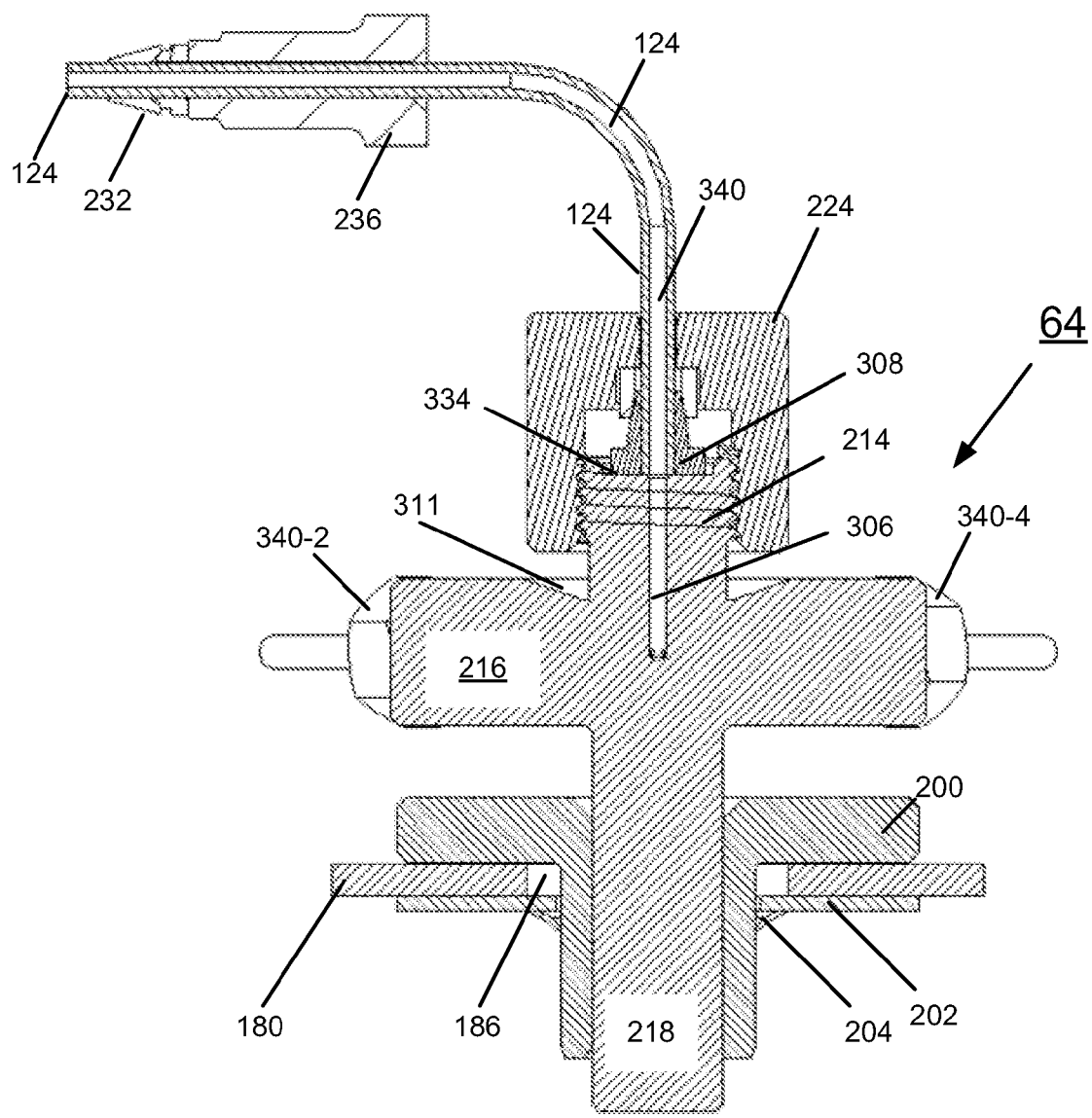
FIG. 11C shows another cross-section view of the manifold shown in accordance with a cross-section taken along line B-B in FIG. 11A.

FIG. 11B and FIG. 11C show side views of the manifold 64 mounted on the manifold bracket 180 in accordance with the cross-sections A-A and B-B, respectively, in FIG. 11A. The threaded interior of the cap 224 is threaded onto the threaded upper portion 214 of the manifold 64. The mouth 330 (FIG. 10E) of the outlet port 72 (FIG. 10E) receives the flat-bottom ferrule 308 and end of the tubing 124. Tightening of the cap 224 urges the leading surface of the flat-bottom ferrule 308 and the end of the tube 124 against the bottom surface 334 in the mouth 330 of the outlet port 72. The cap 224 can be hand-tightened. After the tightening, the circular end of the tube 124 abuts this bottom surface 334 and surrounds the outlet conduit 306, with the bore 340 of the tubing 124 aligning with the outlet conduit 306. The tubing 124 and the outlet conduit 306 may have matching inner diameters.

Figure 12A:
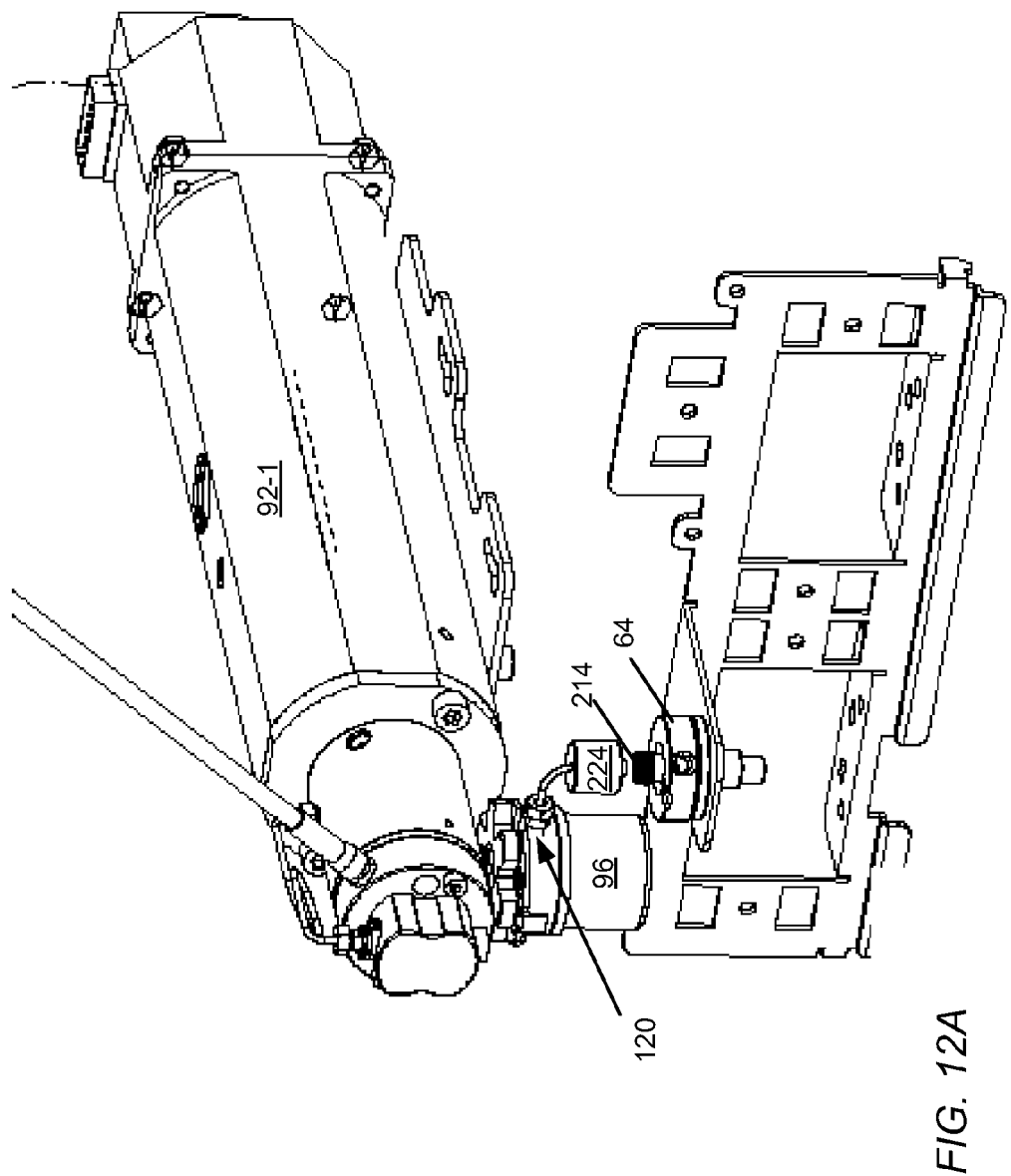
FIG. 12A, FIG. 12B, FIG. 12C are views illustrating a sequence of detaching the inlet check valve from the primary pump.
Figure 12B:
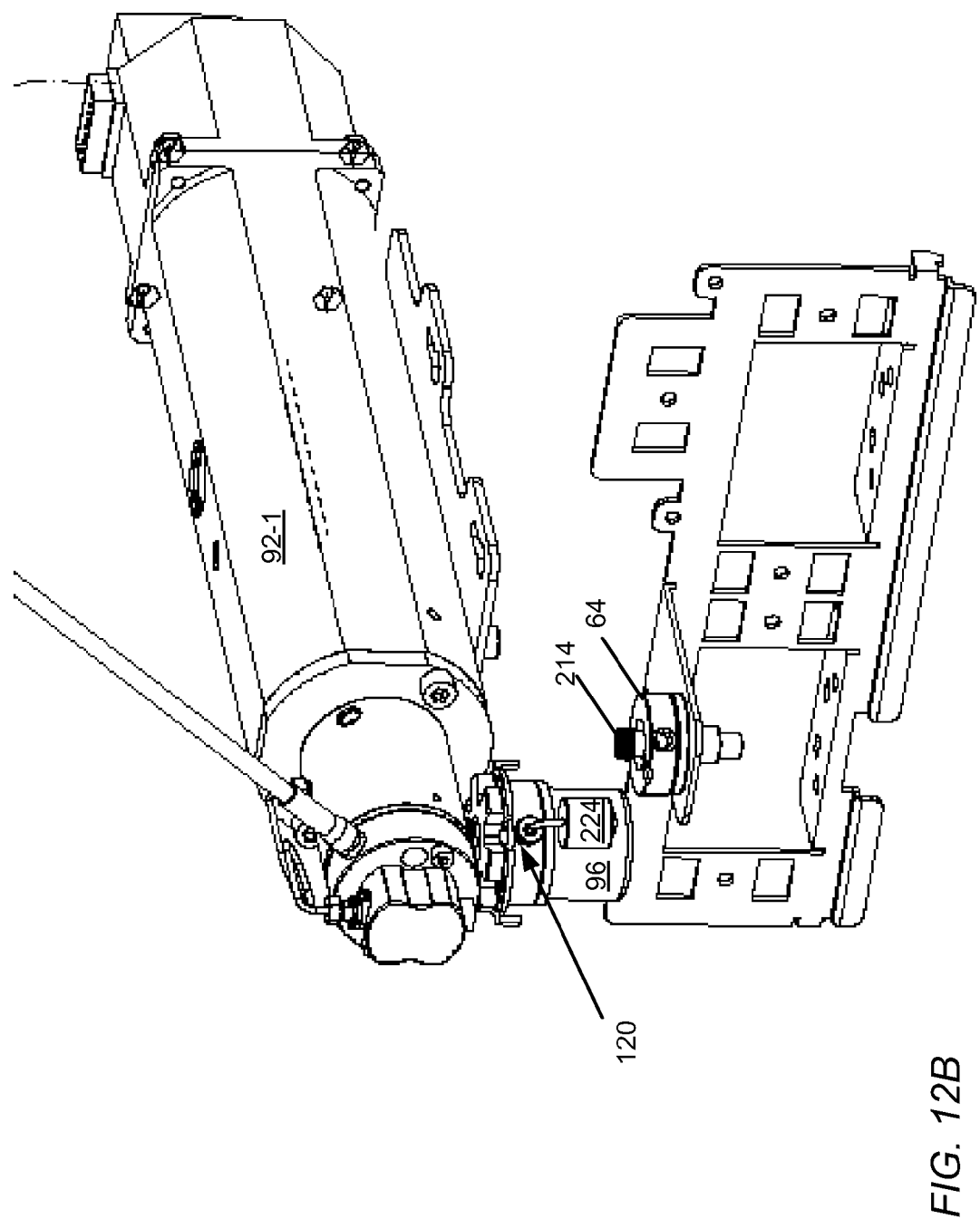
Figure 12C:
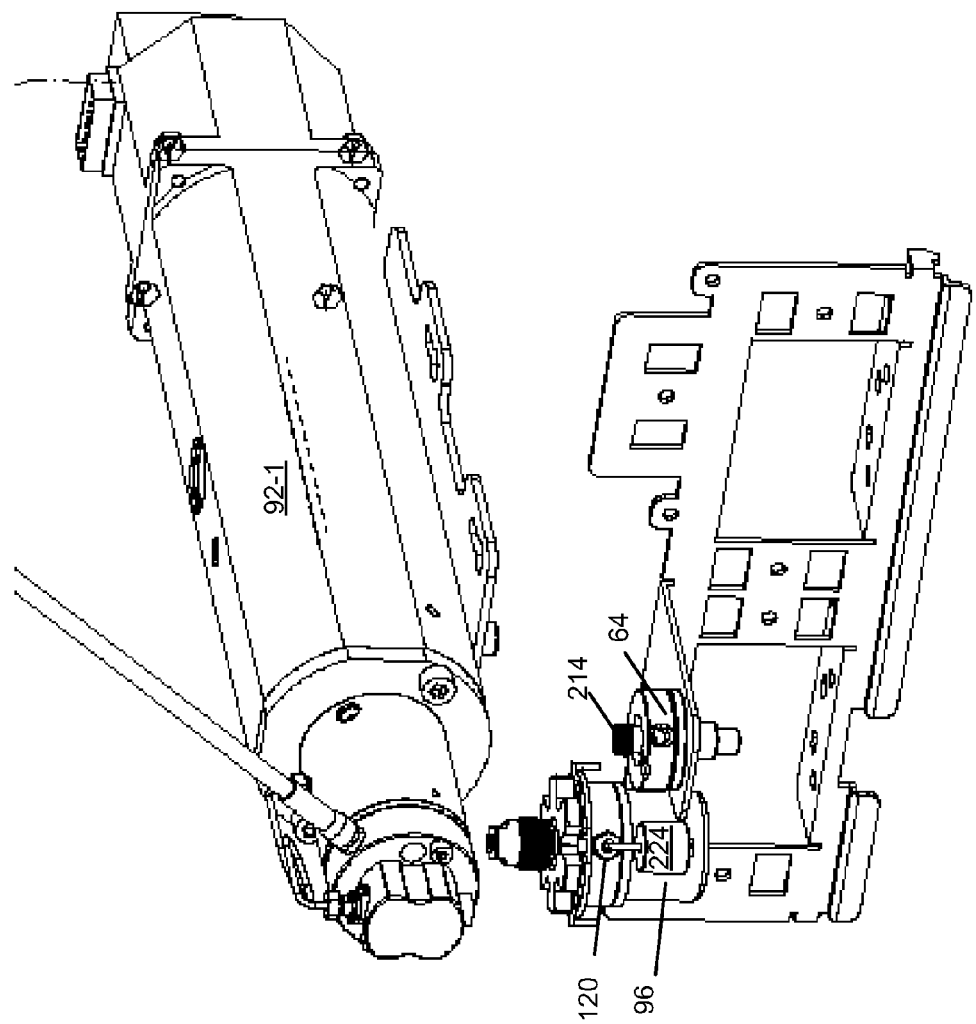

FIG. 12A, FIG. 12B, FIG. 12C illustrate an example of a disassembly process in which the inlet check valve 96 is detached from the primary pump 92-1. The process may be performed during preventative maintenance or cleaning of the solvent delivery system 12. The configuration of the outlet tube 124, fittings 220 to the check valve inlet 96, and cap 224 connected to the manifold outlet 72 eases maintenance of the solvent delivery system 12.

FIG. 12A shows a first step of unscrewing the cap 224 from threaded outer diameter 214 of the outlet port 72. The ability to detach the inlet check valve 96 from the manifold 64 by unscrewing the cap 224 is generally a more convenient mechanism for separating the components than loosening other types of fittings. In addition, the cap 224 being hand-tightened may advantageously induce a user to undo this attachment first in the disassembly process. At this stage, the inlet check valve 96 remains attached to the primary pump 92-1 and the fitting 120 remains attached to the inlet check valve 96. FIG. 12B shows the inlet check valve 96 rotated approximately 45 degrees from its position in FIG. 12A. At the position, the inlet check valve 96 can be separated from the primary pump 92-1, as shown in FIG. 12C. Throughout the disassembly process, the upright orientation of the manifold 64 remains unchanged.

Figure 13:
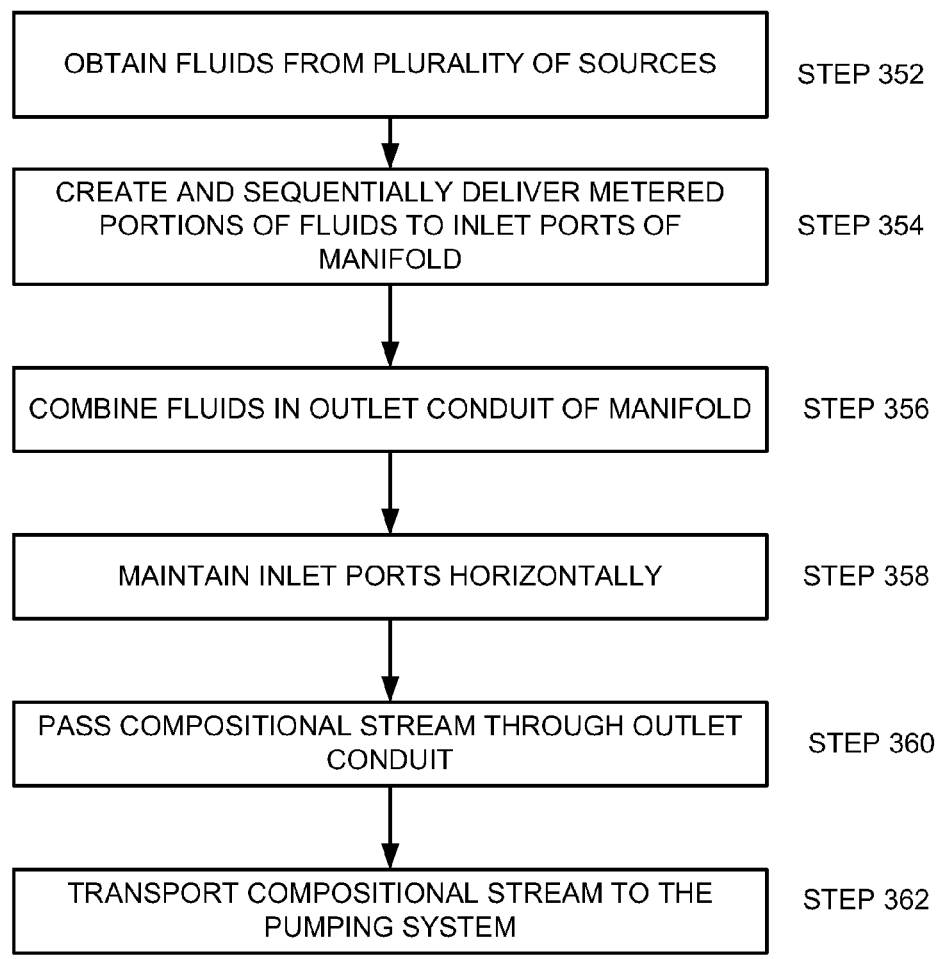
FIG. 13 is a flow diagram of an embodiment of a process of low-pressure mixing of fluids.

FIG. 13 shows an embodiment of a process 350 of low-pressure mixing of fluids. The description of the process 350 also refers to features shown in FIG. 2 and FIG. 10. It is to be understood that the process 350 is not to be limited to the particular order in which its steps are described; such steps can occur in a different order and/or simultaneously. At step 352, solvents or fluids are obtained from a plurality of sources. The GPVs 60 meter (step 354) the proportions of the fluids being transported to the inlet ports 68 of the manifold 64. The fluids pass (step 356) from the inlet ports 68 to the internal outlet conduit 306 of the manifold 64. These inlet ports 68 are maintained (step 358) in a substantially horizontal orientation to moderate cross-flow of fluids between inlet ports 68 when delivering the fluids to the outlet conduit 306. A compositional stream of slices or packets passes (step 360) through the outlet conduit 306 and exits the manifold 64 through the output port 72. The compositional stream is transported (step 362) from the outlet port 72 of the manifold into the inlet check valve 96 of the pumping system 20.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, RAM, ROM, an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the invention has been shown and described with reference to specific preferred embodiments, it should be understood by those skilled in the art that various changes in form and detail may be made therein without departing from the spirit and scope of the invention. Examples of such variations include, but are not limited to: having the outlet conduit 306 in the same horizontal plane as the inlet conduits 310 (rather than orthogonal to the inlet conduits); angling the inlet ports 68 and inlet conduits 310 up or down to feed into the outlet conduit (rather than lying entirely in a horizontal plane); and having the inlet conduits 310 feed into the outlet conduit from above (rather than from below) with the outlet port 72 being at the bottom of the manifold 64 instead of at the top.

What is claimed is:

1. An apparatus for combining fluids, comprising:
   a pipe-shaped portion having an outlet port at one end and an internal outlet conduit providing an internal fluidic passageway to the outlet port, the pipe-shaped portion having, in a side thereof, a plurality of openings into the internal outlet conduit; and
   a main body having an outer diameter with a plurality of inlet ports for receiving microfluidic tubing, each inlet port including a tube receptacle ending at a tip and an inlet conduit that directly connects the tip to one of the plurality of openings in the side of the pipe-shaped portion, thereby providing a direct internal fluidic passageway from the tip to the outlet conduit, each of the plurality of inlet conduits lying in a same plane as every other of the plurality of inlet conduits,
   wherein the outlet conduit has an open end at the outlet port, a closed end opposite the open end, and a plurality of openings in an outer diameter of the outlet conduit near the closed end, and wherein each inlet port is in fluidic communication with one of the openings in the outer diameter of the outlet conduit through the inlet conduit of that inlet port.

2. The apparatus of claim 1, wherein the fluidic passageway provided by each inlet conduit is substantially orthogonal to the fluidic passageway provided by the outlet conduit.

3. The apparatus of claim 1, wherein the inlet ports are symmetrically distributed about an axis parallel to the fluidic passageway of the outlet conduit.

4. The apparatus of claim 1, wherein the outlet port has a threaded outer diameter.

5. The apparatus of claim 4, further comprising:
   a tube fitting for mating with a fluidic inlet valve of a pumping unit;
   a cap with a threaded inner diameter for mating with the threaded outer diameter of the outlet port, the cap further comprising a surface with a central opening; and
   tubing connecting the central opening of the cap to the tube fitting.

6. The apparatus of claim 1, wherein the tube receptacle of each inlet port is a receptacle for a tube fitting and has a tapered conical tip that meets the inlet conduit of that inlet port.

7. An apparatus for combining fluids, comprising:
   a pipe-shaped portion having an outlet port at one end and an internal outlet conduit providing an internal fluidic passageway to the outlet port, the pipe-shaped portion having, in a side thereof, a plurality of openings into the internal outlet conduit; and
   a main body having an outer diameter with a plurality of inlet ports for receiving microfluidic tubing, each inlet port including a tube receptacle ending at a tip and an inlet conduit that directly connects the tip to one of the plurality of openings in the side of the pipe-shaped portion, thereby providing a direct internal fluidic passageway from the tip to the outlet conduit, each of the plurality of inlet conduits lying in a same plane as every other of the plurality of inlet conduits, wherein the outlet port has a threaded outer diameter.

8. The apparatus of claim 7, wherein the fluidic passageway provided by each inlet conduit is substantially orthogonal to the fluidic passageway provided by the outlet conduit.

9. The apparatus of claim 7, wherein the inlet ports are symmetrically distributed about an axis parallel to the fluidic passageway of the outlet conduit.

10. The apparatus of claim 7, wherein the tube receptacle of each inlet port is a receptacle for a tube fitting and has a tapered conical tip that meets the inlet conduit of that inlet port.

11. An apparatus for combining fluids, comprising:
a pipe-shaped portion having an outlet port at one end and an internal outlet conduit providing an internal fluidic passageway to the outlet port, the pipe-shaped portion having, in a side thereof, a plurality of openings into the internal outlet conduit;
a main body having an outer diameter with a plurality of inlet ports for receiving microfluidic tubing, each inlet port including a tube receptacle ending at a tip and an inlet conduit that directly connects the tip to one of the plurality of openings in the side of the pipe-shaped portion, thereby providing a direct internal fluidic passageway from the tip to the outlet conduit, each of the plurality of inlet conduits lying in a same plane as every other of the plurality of inlet conduits;
a tube fitting for mating with a fluidic inlet valve of a pumping unit;
a cap with a threaded inner diameter for mating with the threaded outer diameter of the outlet port, the cap further comprising a surface with a central opening; and
tubing connecting the central opening of the cap to the tube fitting.

12. The apparatus of claim 11, wherein the fluidic passageway provided by each inlet conduit is substantially orthogonal to the fluidic passageway provided by the outlet conduit.

13. The apparatus of claim 11, wherein the inlet ports are symmetrically distributed about an axis parallel to the fluidic passageway of the outlet conduit.

14. The apparatus of claim 11, wherein the tube receptacle of each inlet port is a receptacle for a tube fitting and has a tapered conical tip that meets the inlet conduit of that inlet port.

15. An apparatus for combining fluids, comprising:
a pipe-shaped portion having an outlet port at one end and an internal outlet conduit providing an internal fluidic passageway to the outlet port, the pipe-shaped portion having, in a side thereof, a plurality of openings into the internal outlet conduit; and
a main body having an outer diameter with a plurality of inlet ports for receiving microfluidic tubing, each inlet port including a tube receptacle ending at a tip and an inlet conduit that directly connects the tip to one of the plurality of openings in the side of the pipe-shaped portion, thereby providing a direct internal fluidic passageway from the tip to the outlet conduit, each of the plurality of inlet conduits lying in a same plane as every other of the plurality of inlet conduits,
wherein the tube receptacle of each inlet port is a receptacle for a tube fitting and has a tapered conical tip that meets the inlet conduit of that inlet port.

16. The apparatus of claim 15, wherein the fluidic passageway provided by each inlet conduit is substantially orthogonal to the fluidic passageway provided by the outlet conduit.

17. The apparatus of claim 15, wherein the inlet ports are symmetrically distributed about an axis parallel to the fluidic passageway of the outlet conduit.

18. The apparatus of claim 15, wherein the outlet port has a threaded outer diameter.

19. The apparatus of claim 15, further comprising:
a tube fitting for mating with a fluidic inlet valve of a pumping unit;
a cap with a threaded inner diameter for mating with the threaded outer diameter of the outlet port, the cap further comprising a surface with a central opening; and
tubing connecting the central opening of the cap to the tube fitting.

* * * * *